United States Patent
Ren et al.

(10) Patent No.: US 6,509,035 B1
(45) Date of Patent: Jan. 21, 2003

(54) ORAL PREPARATION OF COENZYME A USEFUL FOR LOWERING BLOOD LIPID AND A METHOD PRODUCING FOR SAME

(75) Inventors: Genfu Ren, Shanghai (CN); Guijun Fei, Shanghai (CN)

(73) Assignee: Shanghai Materia Medica Bioengineering Institute, Shanghai (CH)

( * ) Notice: Subject to any disclaimer, the term of this patent is extended or adjusted under 35 U.S.C. 154(b) by 0 days.

(21) Appl. No.: 09/633,461

(22) Filed: Aug. 8, 2000

(30) Foreign Application Priority Data

Aug. 16, 1999 (CN) .......................... 99113983 A

(51) Int. Cl.[7] .............. A61K 9/20; A61K 9/68
(52) U.S. Cl. .............. 424/464; 424/400; 424/451; 424/489; 514/960; 514/962
(58) Field of Search .............. 424/400, 451, 424/464, 489; 514/960, 962

(56) References Cited

U.S. PATENT DOCUMENTS 5,662,934 A * 9/1997 Najarian ............ 424/464
6,235,311 B1 * 5/2001 Ullah et al. ............ 424/472
6,245,797 B1 * 6/2001 Winokur ............ 514/406

FOREIGN PATENT DOCUMENTS

| JP | 8245352 | 9/1996 |
| WO | 9320805 | 10/1993 |
| WO | 9415592 | 7/1994 |
| WO | 9640167 | 12/1996 |

OTHER PUBLICATIONS

English translation of the abstract of JP 8–245352 dated Sep. 24, 1996.

* cited by examiner

Primary Examiner—Thurman K. Page
Assistant Examiner—Charesse Evans
(74) Attorney, Agent, or Firm—Ladas & Parry

(57) ABSTRACT

A coenzyme A oral preparation, a producing method and a use for treating hyperlipemia thereof are disclosed. The coenzyme A oral preparation of the present invention is tablet, capsule, powder, granule or microcapsule, which is consisted of coenzyme A, an antioxidant, an acidic buffer or acidifier and one or more pharmaceutically acceptable excipient(s).

19 Claims, No Drawings

ORAL PREPARATION OF COENZYME A
USEFUL FOR LOWERING BLOOD LIPID
AND A METHOD PRODUCING FOR SAME

FIELD OF THE INVENTION

The present invention relates to a medicament useful for treating hyperlipemia and a producing method thereof. More specifically, the present invention relates to an oral preparation of coenzyme A (CoA) and a producing method thereof.

BACKGROUND OF THE INVENTION

CoA is a ubiquitous active substance found in organisms and is consisted of pantothenic acid, adenine, ribose, cysteamine and phosphoric acid. It is the coenzyme for acetylation reaction in vivo, and plays an extremely important role in metabolism of carbohydrates, lipids and proteins. For example, it is essential for the process of tricarboxylic acid cycle, storage of hepatic glycogen, synthesis of acetylcholine, decrease of the amount of cholesterol, regulation of the level of plasma lipid and synthesis of steroids. CoA significantly alleviates the symptoms of anorexy and hypodynamia of patients and has been used as helper medicament for treatment of diseases such as arteriosclerosis, chronic arteritis, myocardial infarction, myocarditis, various liver diseases, leucopenia, thrombopenic purpura, acute anuria induced by chronic renal insufficiency, nephrotic syndrome, uremia, neonatal anoxia and diabetes acidosis, etc. Because CoA is susceptible to the dephosphorylation by phosphoesterase in enteric tract, the only route of CoA administration has been by injection up to now, which is pain and inconvenient for patients and increases cost. Therefore, the use of CoA is limited.

SUMMARY OF THE INVENTION

The object of the present invention is to overcome such disadvantages of exsisting CoA preparations. Therefore, the first aspect of the invention provides an oral absorbable CoA preparation with stable therapeutic effect; the second aspect of the invention provides a method for preparing the said CoA oral preparation; and the third aspect of the invention provides a use of the said CoA oral preparation for treating hyperlipemia; and the fourth aspect of the invention provides a method of treating hyperlipemin in an individual with the said CoA oral preparation.

DETAILED DESCRIPTION OF THE INVENTION

The Oral CoA preparation of the present invention can be tablet, capsule, powder, granule, and microcapsule consisting of 0.04–9.99% active ingredient CoA, 0.4–99.55% an antioxidant, 0.4–99.55% an acidic buffer or acidifier and 0–98.99% a pharmaceutically acceptable excipient(s).

The method for preparing the CoA oral preparation of the present invention, 1 portion of CoA was added to 20–800 portions of salt-free water, and then 0–20 portions of an antioxidant, 1–20 portions of an acidic buffer or acidifier, 0–40 portions of an extender were added to dissolve and then lyophilized to obtain the raw material (a lyophilized powder) for making the preparations of the invention. Based on the amount of CoA lyophilized powder, 1–2489 portions of an antioxidant, and 0–2489 portions of an acidic buffer or acidifier were added to the lyophilized powder and mixed uniformly, and then formulated with a pharmaceutical excipient(s) to form CoA oral tablet, capsule, granule, powder or microcapsule according to a conventional process.

Tablet, capsule, granule, powder and microcapsule of the present invention can be formulated according to following conventional process:

To the raw material as botained above containing one portion of CoA, 1–2489 portions of an antioxidant, 0–2489 portions of an acidic buffer or acidifier, and a suitable amount of binder, disintegrant and extender are added and mixed uniformly, then starch syrup is added. The resulting mixture then is granulated, tableted and dried to form tablets, each containing 10–500 units of CoA.

To the raw material as obtained above containing one portion of CoA, 1–2489 portions of an antioxidant, 0–2489 portions of an acidic buffer or acidifier, and a suitable amount of binder, disintegrant and extender are added and mixed uniformly. Then the resulting mixture as obtained can be packed as powder according to desired dosages. Alternathply a suitable amount of starch syrup can be added to the mixture followed by granulating, drying and sterile packing to form granules containing 10–500 units of CoA per package. Furthermore capsules with 10–500 units of CoA per capsule can be obtained after filling the dried granules into capsule shells and sealing.

To the raw material as obtaimed above containing one portion of CoA, 1–2489 portions of an antioxidant and 0–2489 portions of an acidic buffer or acidifier are added and then ground and mixed uniformly.

The resulting mixture is then added to a solution of ethyl cellulose (EC) in isopropanol and then EC microcapsules of CoA are obtained after spray drying.

The antioxidant of the invention can be any pharmaceutically acceptable one such as Vitamin C, sulfourea, glutathione, alanine, cystein, etc.

The acidic buffer of the invention can be any pharmaceutically acceptable one such as sodium dihydrogen phosphate, potassium dihydrogen phosphate; and the acidifier of the invention can be any pharmaceutically acceptable one such as citric acid, aspartic acid, glutamic acid, folic acid.

The pharmaceutically acceptable excipients useful for the invention include conventional binder such as starch, hydroxyl propyl starch, modified starch, pregelatinized starch, dextrin, sugar powder, microcrystalline cellulose, gelatin syrup, and PVP mucilago; disintegrant such as sodium carboxymethyl starch, starch and microcrystalline cellulose; lubricant such as modified starch, microcrystalline cellulose, micro-powder silicon gel and aluminum hydroxide; and extender such as starch and derivative thereof, celluloses and derivatives thereof, inorganic compounds, organic salts and hexonic acids or pentitols.

The clinical administration dosage of CoA of the invention is 10–500 units of CoA per day. One mg of pure CoA corresponds to 413 units, while commercially available CoA of pharmaceutical grade is of about 250 units per mg, i.e. 100 units of CoA weighs about 0.4 mg.

Enteric phosphoesterase usually can inactivate enteric CoA by dephosphorylation at its 3-position quickly. The optimal pH of phosphoesterase is 9.8. An oxidated type of CoA is more easily be inactivated than the reduced type. Although not bound by any theory, it is contemplated that the pvesent invention works by inhibiting the enzyme reaction process of the inactivation of enteric CoA. In the preparation of the present invention, an antioxidant was added in order to maintain the reduced state of CoA; and an acidic buffer or acidifier was added to form a slightly acidic micro-environment in enteric tract after oral administration of CoA, which lead to the inhibition of degradation of CoA by phosphoesterase so that CoA can be absorbed before inactivation. The oral preparation of the present invention therefore exerts similar biological effect as a injectable preparation.

Pharmacodynamic experiments using the CoA oral preparation of the present invention and an injectable preparation of CoA on thrombocytopenia:

1. Effect on Peripheral Platelet of Animal

Object: 10 experimental dogs were used and devided into 2 groups of 5 to which oral or injection preparations of CoA was administered, respectively. Their peripheral platelet samples were taken and tested at intervals to observe the differences between before and after administration.

Dosage of CoA: Oral administration group, 100 units per time, twice per day. Injection administration group, 35 units per time, twice per day.

Result: Statistical analysis were carried out on the changes of the number of platelets before and after the administration of CoA to dogs by individual comparison test. The results are shown in Table 1. It is noted that exogenous CoA can improve the level of platelet in experimental dogs in a short time either administered by oral or injection route. Average increment of $170,800/mm^3$ was observed in the injection administration group on day 8 ($P<0.01$); while $133,000/mm^3$ in the oral administration group on day 6 ($P<0.05$), and thereafter the level of platelet restored to its normal level gradually. It is proved that CoA administered with the oral preparation of the present invention can be absorbed through gastrointestinal tract and exert similar biological effect as injectable CoA.

TABLE 1

Effect of CoA on platelet of experimental dogs (unit: $10,000/mm^3$)

| Sampling Time | 1 | 3 | 6 | 8 | 10 | 13 |
|---|---|---|---|---|---|---|
| Injection adminstration | | | | | | |
| Average increment of platelet $\overline{X}$ | 0.28 | 7.44 | 5.48 | 17.08 | 11.36 | 3.68 |
| Standard deviation Sd | 6.10 | 7.56 | 1.93 | 2.82 | 2.98 | 4.20 |
| t | 0.445 | 0.984 | 2.84 | 6.08 | 3.81 | 0.86 |
| p | | | <0.05 | <0.01 | <0.05 | |
| Oral adminstration | | | | | | |
| Average increment of platelet $\overline{X}$ | 8.64 | 8.06 | 13.3 | 4.25 | 1.96 | -2.52 |
| Standard deviation Sd | 2.81 | 4.89 | 4.64 | 3.94 | 3.38 | 3.60 |
| t | 3.07 | 1.65 | 2.87 | 1.08 | 0.58 | 0.65 |
| p | <0.05 | | <0.05 | | | |

2. Effect on human thrombocytopenia induced by chemicals

Object: Individuals with platelet counter $<80,000/mm^3$ induced by chemicals were chosen, wherein 15 cases were simple thrombocytopenia patients, 10 male and 5 female, aged from 29 to 56; and 15 cases were patients with decreased platelet and leukocyte at the same time, 6 male and 9 female, aged from 31 to 66.

Oral dosage of CoA: one tablet per time, 35 units per tablet, administered on empty stomach three times daily. The course of treatment lasts one month.

The difference of platelet between before and after administration was determined. The administration of any other medicaments was stopped during the treatment, while the working and living environments did not change.

Result: 15 patients with simple thrombocytopenia and 15 patients with decrease of both platelet and leukocyte were compared by individual comparison test, i.e. the difference of platelet between one month after the administration and before administration. (See Table 2)

It was shown that CoA tablet can notably increase the amount of platelet of thrombocytopenia patients induced by chemicals, no matter they were simple thrombocytopenia patients or patients with decrease of both platelet and leukocyte. It showed an extremely evident statistical significance ($P<0.001$). With regard to the patients with simple thrombocytopenia, the average increment was $26,900/mm^3$ after administration and 86.6% of them have increment more than $20,000/mm^3$. With regard to the patients with decrease of both platelet and leukocyte, the average increment are $24,200/mm^3$ after administration and 66.6% of them have increment more than $20,000/mm^3$. No toxic or side effect was found in any case. Most of the patients felt well after administration and had enhanced appetite.

TABLE 2

Effect of CoA on human thrombocytopenia induced by chemicals (Unit: $10,0/mm^3$)

| Disease | Patient number | Average increment of platelet $\overline{X}$ | Standard deviation Sd | t | P |
|---|---|---|---|---|---|
| Simple thrombocytopenia | 15 | 2.69 | 0.25 | 10.88 | <0.001 |
| Decrease of both platelet and leukocyte | 15 | 2.42 | 0.27 | 9.30 | <0.001 |

The result of the above experiment shows that there is no statistically significant difference between the biological effects caused by the oral CoA of the invention and the injectable preparation. Therefore, it is considered that oral CoA can be absorbed through gastrointestinal tract and exert equivalent biological effect in organisms.

The another object of the present invention is directed to a new use of CoA for lowering blood lipid.

It is well known that hypertension and hyperlipemia is the main predisposing cause of cardio-cerebrovascular diseases. As to cholesterol in hyperlipemia, in addition to nicotinic acid and inositol, Lovostatin is also effective for its inhibition effect on the synthesis of endogenic cholesterol. But there are no safe and effective medicament aiming at triglyceride. Though atromides and their derivatives recommended by WHO can reduce the concentration of triglyceride in blood, they are particularly not suitable for the senile patients with hypertriglyceridemia because of their side effect on major organs such as liver and kidney, thus clinical use of this kind of medicaments is limited. Moreover, the price of the existing lipid-lowering medicaments are high and these medicaments need long-term administration which is an economic burden to the patients.

CoA can improve the lipid metabolism of type $II_b$ and IV hyperlipemia patients. It can make the electrophoresis of lipid protein normal quickly after eating lipid-rich food, but have no such effect on normal person. It can be deduced that these two type of hyperlipemia may be related to the lack of CoA. CoA is a ubiquitous coenzyme involving in acetylation reaction in all living cells. It relates to a large number of metabolism process in organisms and is very important in these process. It participates in metabolism of carbohydrates, lipid, protein and energy. CoA is indispensable during β-oxidation of the metabolism of fatty acids where they decompose to acetyl-CoA step by step. Then acetyl-CoA enter into tricarboxylic acid cycle in mitochondrion wherein it is oxidized into $H_2O$ and $CO_2$ and releases energy. The blood lipid-lowering action of exogenous CoA may be related to this. CoA in CoA oral preparation is biogenic substance prepared by biotechnology and no side effect are found during long-term administration. It has the advantages of nontoxicity, no side effect, smaller dosage and cheaper cost compared with the existing blood lipid-lowering medicaments (in particualr, triglyceride-lowering agent).

Experimental result of the effect of CoA on serum triglyceride and cholesterol in the patients with hyperlipemia:

Object: Individuals with plasma lipid more than 90% of upper limit of normal person were chosen, i.e. serum cholesterol >230 mg %, or triglyceride >160 mg %, 39 patients in total, 14 male, aged from 28-65; 25 female, aged from 32 to 70.

Oral dosage of CoA: one tablet per time, 35 units per tablet, administered on empty stomach three times daily. Three months was used as a course of treatment. During the course of the administration, the patients had diet same as the normal and stopped the administration of any other lipid-lowering medicament.

Measurement of plasma lipid: venous blood samples were taked from 12–14 hrs-fasting patients before administration and one month and 3 months after administration. Concentration of serum cholesterol and triglyceride were measured after isolation of serum. In the meantime, each patients' medical history was inquired, blood pressure was measured and liver function was determined.

Result (1) Effect on triglyceride: Statistical analysis were carried out on the difference of the concentration of serum triglyceride of hyperlipemia patients between before and after the administration of CoA by individual comparison test. The result is shown in Table 3.

It showed that the concentration of serum triglyceride decreased notably 1 and 3 months after administration of CoA tablet. It had extremely evident statistical significance (P<0.001). The average decrements were 64.2 mg % and 75.5 mg %, respectively In 26 of the 39 patients one month after administration, triglyceride decreased more than 20 mg %, the effective ratio was 66.7%, and the average decrement was 112.2 mg %; 4 of them had no change, and 9 of them showed a little increment compared with those of before administration.

Effective ratio of lowering triglyceride in 37 patients three months after administration was 70.3%, the average decrement was 118 mg %, and the maximum effective one had the decrement of 290% mg; 4 of them had no effect and 7 of them showed a little increment.

(2) Effect on cholesterol: Statistical analysis was carried out on the difference of the concentration of serum cholesterol of patients with hyperlipemia between before and after the administration of CoA by individual comparison test. The result is shown in Table 4.

It showed that the concentration of serum cholesterol decreased notably 1 and 3 months after administration of CoA tablet. It had extremely evident statistical significance (P<0.001). The average decrement was 25.7 mg % and 22.1 mg %, respectively.

One month and three months after administration, the patients with cholesterol decrement more than 20 mg % were 56.4% and 48.6%, respectively, the average decrease of cholesterol in effective patients was 44.4 mg % and 56.1% mg, respectively, and there were 2 and 3 of the cases showed a little increment in cholesterol concentration, respectively.

No toxic or side effect were found after three months continuous administration in any case. No side effect was found on the function of liver or kidney and blood pressure. Part of the patients felt well after administration and had enhanced appetite.

It should be indicated that blood lipid-lowering CoA is only aimed at type $II_b$ and IV hyperlipemia (i.e. hypertriglyceridemia and hypertriglyceridemia with hyperchesterolemia complication), and these two type of patients accounts for 80–85% of all hyperlipemia patients. Since the patients chosen in the clinical trial had nor been typed, it is obvious that the effective rate of CoA on type $II_b$ and IV hyperlipemia patients will be higher.

TABLE 3

The difference of triglyceride concentration between before and after oral administration of CoA (mg %)

| Course | Number of cases | Average difference between before and after administration | Standard deviation Sd | t | P |
|---|---|---|---|---|---|
| One month | 39 | 64.2 | 14.5 | 4.43 | <0.001 |
| Three months | 37 | 75.5 | 15.9 | 4.75 | <0.001 |

TABLE 4

The difference of serum cholesterol concentration between before and after oral administration of CoA (mg %)

| Course | Number of cases | Average difference between before and after administration | Standard deviation Sd | t | P |
|---|---|---|---|---|---|
| One month | 39 | 25.7 | 4.8 | 5.38 | <0.001 |
| Three months | 37 | 22.1 | 5.6 | 3.90 | <0.001 |

It is shown from the experiment that oral administration of CoA tablet can effectively lower the level of serum triglyceride and cholesterol of patients with hyperlipemia, especially those with type $II_b$ and IV hyperlipemia. Its effective rate and decrement are similar to those of serval medicaments recommended by FDA of USA such as atromide and pantethine of Japan. Moreover, it has the advantage of nontoxicity, cheap cost, and small dosage.

The oral preparation of CoA and its method of production of the present invention can solve the problem of inactivation of CoA administrated by oral route and provide the possibility of treating various diseases by oral CoA, which avoid the pain and inconvenience of patients caused by injection and decrease the economic burden of the patients. The new use of CoA for the treatment of hyperlipemia disclosed by the invention has evident effect and expands the medicinal use of CoA. As a biogenic substance, CoA is safer, cheaper and can be used with smaller dosage compared with other similar blood lipid-lowering medicaments. It can also make up for the functional limitation of the existing lipid-lowering medicaments and had a good prospect of development and application.

EXAMPLES

Example 1

Production of a Raw Material of the CoA Oral Preparation 750 ml salt-free water were added to 500,000 units of CoA acetone powder, then 25 g Vitamin C, 25 g sodium dihydrogen phosphate and 25 g mannitol were added in turn, the mixture was stirred to dissolve and lyophilized.

Example 2

Preparation of CoA Oral Tablet 100,000 units of raw material of CoA oral preparation (15.4 g), 45 g Vitamin C, 20 g starch, 10 g sugar powder, 4 g magnesium stearate and a suitable amount of starch syrup(17%).

The above raw materials were ground and mixed uniformly, a suitable amount of starch syrup was added. The resulting mixture then was granulated, dried and then compressed to form tablets with 100 mg punch die.

Example 3

Preparation of CoA Capsule 100,000 units of raw material of CoA oral preparation (15.4 g), 45 g Vitamin C and 39.6 g mannitol were mixed uniformly to form 1000 capsules.

Example 4

Preparation of CoA Oral Powder or Granule 45 g Vitamin was added to 100,000 units of raw material of CoA oral preparation (15.4 g), and then other various pharmaceutically acceptable excipients were added to form 10~500 units of CoA/dosage and finally sterile packing.

Example 5

Preparation of CoA Enteric Capsule 100,000 units of raw material of CoA oral preparation (15.4 g), 70 g Vitamin C, 10 g sodium dihydrogen phosphate and 19.6 g mannitol were mixed uniformly to form 1000 enteric capsules.

Example 6

Preparation of CoA Oral Tablet 35,000 units of raw material of CoA oral preparation, 50 g glutathion, 10 g $NaH_2PO_4$, 15 g starch, 10 g sugar powder, 4 g magnesium stearate, and a suitable amount of starch syrup(17%).

The above raw materials were ground and mixed uniformly, and a suitable amount of starch syrup was added. The resulting mixture then was granulated, dried and then compressed to form tablets with 100 mg punch die, each comprising 35 units of CoA.

Example 7

Preparation of CoA Capsule 50,000 units of raw material of CoA oral preparation, 5 g cystein, 5 g sodium dihydrogen phosphate and 89.6 g mannitol were mixed uniformly to form 1000 capsules, each comprising 50 units of CoA.

Example 8

Preparation of CoA Oral Enteric Capsule 100,000 units of raw material of CoA oral preparation, 10 g glutathion, 70 g sodium dihydrogen phosphate and 19.6 g mannitol were mixed to form 1000 enteric capsules.

Example 9

Preparation of CoA Microcapsule 100,000 units of raw material of CoA oral preparation, 70 g Vitamin C and 10 g sodium dihydrogen phosphate were ground to form powder, mixed uniformly and the resulting mixture is then added to a solution of EC in isopropanol and then CoA's EC microcapsules were obtained after spray drying.

What is claimed is:

1. A Coenzyme A oral preparation, comprising 0.04–9.99% Coenzyme A, 0.4–99.55% of an antioxidant, 0.4–99.55% of an acidic buffer or acidifier and 0–98.99% of a pharmaceutically acceptable excipient or excipients.

2. The Coenzyme A oral preparation of claim 1, wherein the preparation is in the form of a tablet, capsule, granule, powder or microcapsule.

3. The Coenzyme A oral preparation of claim 1, wherein the antioxidant is selected from the group consisting of vitamin C, sulfourea, glutathione, alanine and cystein.

4. The Coenzyme A oral preparation of claim 1, wherein the acidic buffer is selected from the group consisting of sodium dihydrogen phosphate and potassium dihydrogen phosphate, and the acidifier is selected from the group consisting of aspartic acid, glutamic acid, folic acid and citric acid.

5. The Coenzyme A oral preparation of claim 1, wherein the pharmaceutically acceptable excipient is selected from the group consisting of a pharmaceutically acceptable binder, disintegrant, lubricant and extender.

6. The Coenzyme A oral preparation of claim 3, wherein the acidic buffer is selected from the group consisting of sodium dihydrogen phosphate and potassium dihydrogen phosphate, and the acidifier is selected from the group consisting of aspartic acid, glutamic acid, folic acid and citric acid.

7. The Coenzyme A oral preparation of claim 1, wherein the preparation consists essentially of the Coenzyme A, antioxidant, acidic buffer or acidifier, and excipient or excipients.

8. The Coenzyme A oral preparation of claim 6, wherein the preparation consists essentially of the Coenzyme A, antioxidant, acidic buffer or acidifier, and excipient or excipients.

9. A method of producing the Coenzyme A oral preparation of claim 1, comprising the step of mixing 0.04–9.99% Coenzyme A, 0.4–99.55% of an antioxidant, 0.4–99.55% of an acidic buffer or acidifier and 0–98.99% of a pharmaceutically acceptable excipient or excipients.

10. The method of claim 9, wherein the oral preparation is in the form of a tablet, capsule, granule, powder or microcapsule.

11. The method of claim 9, wherein the antioxidant is selected from the group consisting of vitamin C, sulfourea, glutathione, alanine and cystein.

12. The method of claim 9, wherein the acidic buffer is selected from the group consisting of sodium dihydrogen phosphate and potassium dihydrogen phosphate, and the acidifier is selected from the group consisting of aspartic acid, glutamic acid, folic acid and citric acid.

13. The method of claim 9, wherein the pharmaceutically acceptable excipient is selected from the group consisting of a pharmaceutically acceptable binder, disintegrant, lubricant and extender.

14. A method of treating hyperlipemia in an individual, comprising administrating to the individual a therapeutically effective amount of the Coenzyme A oral preparation of claim 1.

15. A method of treating hyperlipemia in an individual, comprising administrating to the individual a therapeutically effective amount of the Coenzyme A oral preparation of claim 3.

16. A method of lowering the level of serum triglyceride and cholesterol in an individual, comprising administrating to the individual a therapeutically effective amount of the Coenzyme A oral preparation according to claim 1.

17. A method of lowering the level of serum triglyceride and cholesterol in an individual, comprising administrating to the individual a therapeutically effective amount of the Coenzyme A oral preparation according to claim 3.

18. The Coenzyme A oral preparation of claim 1, wherein the preparation consists of the Coenzyme A, antioxidant, acidic buffer or acidifier, and excipient or excipients.

19. The Coenzyme A oral preparation of claim 6, wherein the preparation consists of the Coenzyme A, antioxidant, acidic buffer or acidifier, and excipient or excipients.

* * * * *